United States Patent [19]
Schneider et al.

[11] Patent Number: 5,529,677
[45] Date of Patent: Jun. 25, 1996

[54] PLANAR POLAROGRAPHIC SENSOR FOR DETERMINING THE LAMBDA VALUE OF GAS MIXTURES

[75] Inventors: Gerhard Schneider, Vaihingen; Kurt Bayha, Oberriexingen; Hans-Joerg Renz, Leinfelden-Echterdingen, all of Germany

[73] Assignee: Robert Bosch GmbH, Stuttgart, Germany

[21] Appl. No.: 244,273
[22] PCT Filed: Sep. 11, 1993
[86] PCT No.: PCT/DE93/00838
§ 371 Date: May 23, 1994
§ 102(e) Date: May 23, 1994
[87] PCT Pub. No.: WO94/07130
PCT Pub. Date: Mar. 31, 1994

[30]      Foreign Application Priority Data

Sep. 24, 1992 [DE] Germany .............. 42 31 966.8

[51] Int. Cl.⁶ .................................. G01N 27/26
[52] U.S. Cl. ................ 204/425; 204/426; 204/427; 204/429
[58] Field of Search ................. 204/426, 425, 204/427, 429, 153.17, 153.16

[56]           References Cited

U.S. PATENT DOCUMENTS

| | | | |
|---|---|---|---|
| 4,579,643 | 4/1986 | Mase et al. | 204/425 |
| 4,657,659 | 4/1987 | Mase et al. | 204/410 |
| 4,755,274 | 7/1988 | Mase et al. | 204/426 |
| 5,137,615 | 8/1992 | Friese et al. | 204/429 |
| 5,169,512 | 12/1992 | Wiedenmann et al. | 204/426 |

FOREIGN PATENT DOCUMENTS

| | | |
|---|---|---|
| 0194082 | 9/1986 | European Pat. Off. . |
| 0259175 | 3/1988 | European Pat. Off. . |
| 89/02074 | 3/1989 | WIPO . |
| 89/02073 | 3/1989 | WIPO . |
| 89/08840 | 9/1989 | WIPO . |
| 90/04171 | 4/1990 | WIPO . |
| 90/06506 | 6/1990 | WIPO . |
| 90/10862 | 9/1990 | WIPO . |

*Primary Examiner*—Bruce F. Bell
*Attorney, Agent, or Firm*—Spencer & Frank

[57]                ABSTRACT

A planar polarographic sensor for determining the lambda value of gas mixtures, for use with exhaust gases in internal combustion engines, includes a planar ceramic carrier sheet having an outer pumping electrode and an inner pumping electrode respectively arranged on opposite planar sides thereof, and a diffusion barrier. The outer and inner pumping electrodes, and the diffusion barrier are arranged on the planar ceramic carrier sheet so that the measuring gas is fed via the diffusion barrier to the inner pumping electrode. The sensor has front and side edge faces. The diffusion barrier is configured as a diffusion layer at least partially covering the inner pumping electrode and exposed at least at one edge face of the sensor to the measuring gas. A diffusion-free planar region of the sensor is provided with an equalizing layer having the same thickness as the diffusion layer, and the equalizing layer is disposed in the same plane with and adjacent to the diffusion layer.

7 Claims, 5 Drawing Sheets

PLANAR POLAROGRAPHIC SENSOR FOR DETERMINING THE LAMBDA VALUE OF GAS MIXTURES

BACKGROUND OF THE INVENTION

1. Field of the Invention

The invention relates to a planar polarographic sensor.

2. Background Information

Known polarographic sensors serve to determine the lambda value of gas mixtures which defines the ratio of the total oxygen to the oxygen contained in the fuel-air mixture that is combusted in a cylinder, with the sensors determining the oxygen content of the exhaust gas via a change in the boundary flow. Due to cost-effective production methods, the manufacture of planar polarographic sensors that may be produced in ceramic-sheet and screen-print technology has become popular in practice in recent years. These planar polarographic sensors may be produced in a simple and economic manner based on the sheet-like oxygen conducting solid electrolyte bodies made of, for example, zirconium oxide and each coated on both sides with an inner and outer pumping electrode including associated conductors. The inner pumping electrode in this case is disposed in an advantageous manner in the border region of a diffusion channel through which the measuring gas is fed and which serves as gas diffusion resistance.

To improve the reproducibility of the diffusion resistance, DE-OS 38 11 713 proposes to form the diffusion resistance by means of a porous sintering form body without an air gap which is inserted into the unsintered sensor. To accomplish this, a recess is punched out of a solid electrolye sheet and the porous form body is then inserted into the same. In order to supply the measuring gas, a diffusion channel is either guided transversely through the sensor layers to the porous form body or the porous form body is exposed at the end face of the sensor.

EP-A-01 94 082 discloses a planar polarographic sensor whose diffusion resistance is formed by a gap extending parallel to the solid electrolyte body and by a porous insulating layer disposed opposite the gas and covering the electrode. The measuring gas is supplied to the electrode via the gas and the porous insulating layer. The measured gas is supplied to the electrode via the gap and the porous insulating layer.

The production of known planar polarographic sensors is expensive. For example, in order to set the diffusion hole, a punching process is required whose positioning precision is of special significance for the sensor to function. Configuring the diffusion zone with an air gap, on the other hand, requires additional screen printing steps. Each additional screen printing step means an additional drying step and thus increases the chance of altering the length of the substrate. This, in turn, has a negative effect on the positioning precision of the subsequent screen printing steps, which has an adverse effect on reproducibility, especially if a sensor is widened with Nernst cells.

SUMMARY OF THE INVENTION

The polarographic sensor according to the present invention has the advantage of being of an easy-to-produce configuration which allows the screen printing steps of the sensor to be reduced. It is especially advantageous that the diffusion layer is printed on the entire surface of the multiple panels. This allows the individual sensor to be produced very inexpensively. Another advantage is that the diffusion resistance may be set by way of the respective exposed region of the diffusion layer at the end faces of the sensor.

BRIEF DESCRIPTION OF THE DRAWINGS

Three embodiments of the invention are shown in the drawings and are further described, following description.

DETAILED DESCRIPTION OF THE PREFERRED EMBODIMENT(S)

Figure 1:
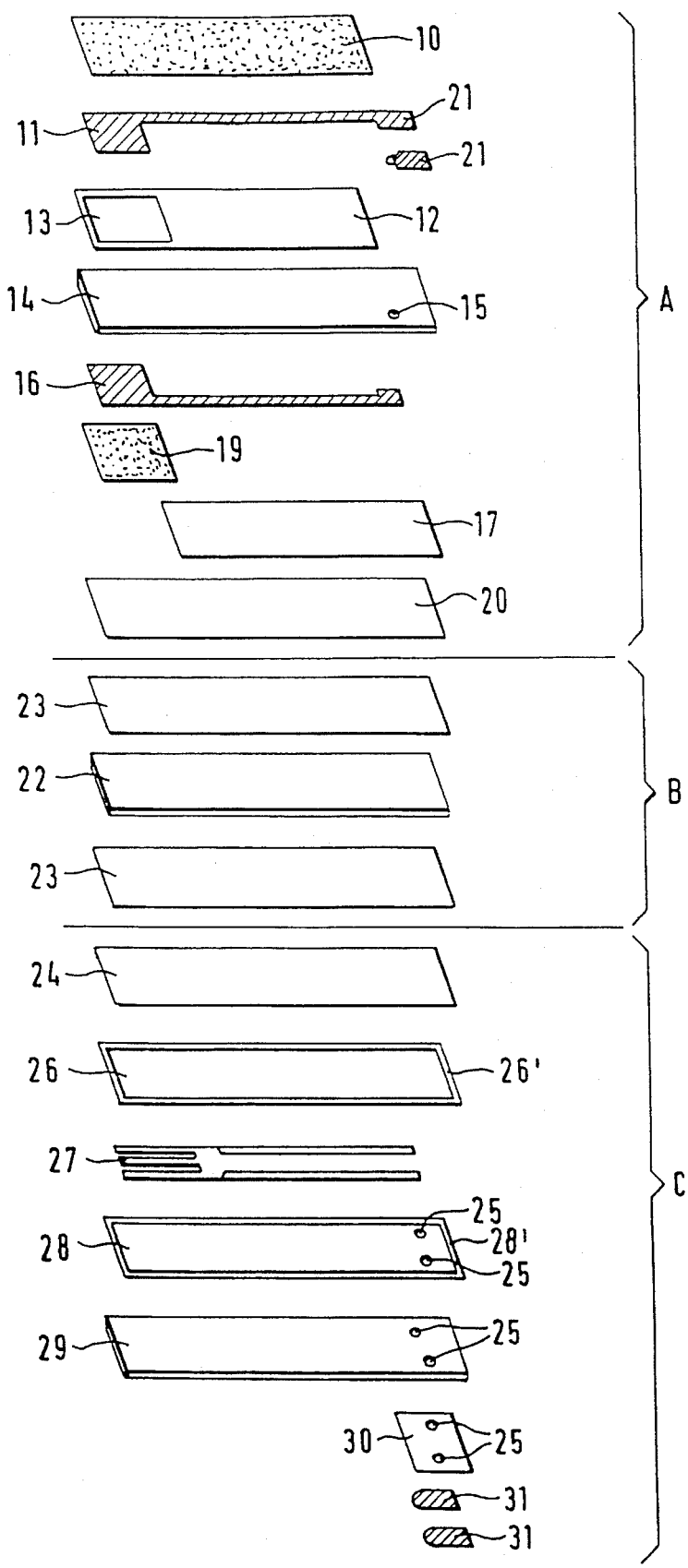
FIG. 1 shows the layout of a first embodiment of a sensor according to the invention.
Figure 2:
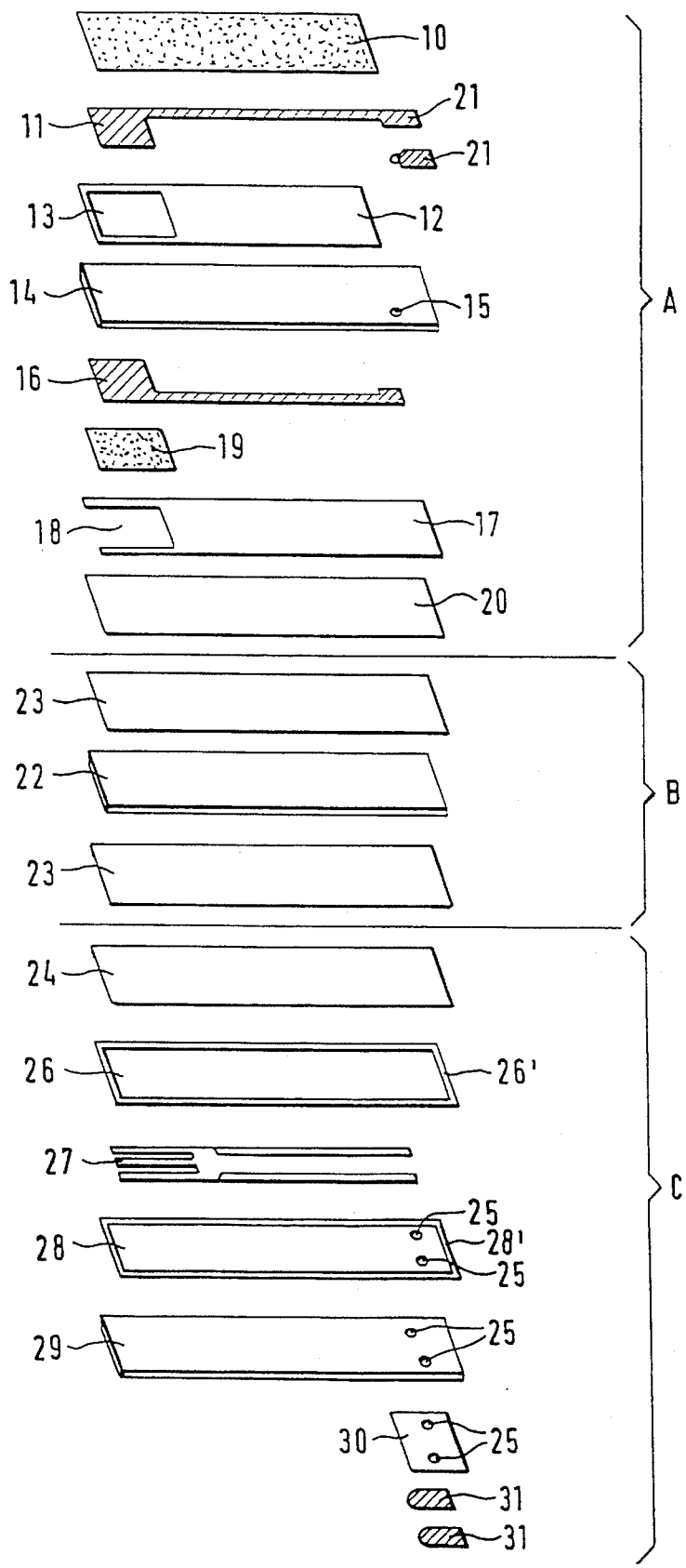
FIG. 2 shows the layout of a second embodiment of a sensor according to the invention.

According to FIGS. 1 and 2, the sensor of the first embodiment comprises a pumping cell A, a thin intermediate sheet B and a heating unit C. Pumping cell A is configured of a first thin solid electrolyte sheet 14 comprising a punched out through-hole 15 and the insulation 12, including a cut-out window 13 on which extends an outer pumping electrode 11. The outer pumping electrode 11 is arranged on the other side of the thin solid electrolyte sheet 14 facing an inner pumping electrode 16 on top of which a porous diffusion layer 19 is placed. An equalizing layer 17 covers the surface of the thin solid electrolyte sheet 14 which is not covered by diffusion layer 19.

The entire surface of the outer pumping electrode 11 is covered with a protective layer. Both electrodes 11, 16 are guided via strip conductors to connectors 21. The protective layer 10 comprises, for example, porous zirconium oxide.

The thin intermediate sheet B serves to stabilize the sensor and comprises a second thin solid electrolyte sheet 22 which is provided at both sides with an interlaminary binding layer 23, respectively.

The heating unit C comprises a thin solid electrolyte sheet 29 having punched-out contact holes 25, a first heating insulation 26 and a second heating insulation 28, each having a gas-tight frame 26' and 28', and heater connectors 31. A further insulation 30 is provided between the thin solid electrolyte sheet 29 and the heater contacts 31. This insulation is also provided with through-holes 25.

A second embodiment is shown is FIG. 2. The embodiment differs from the first embodiment merely in that the diffusion layer 19 is not placed over the entire width of the sensor, but instead, it is limited at the edges of the sensor by equalizing layer 17. The equalizing layer 17 in this case is configured such that a recess 18 is provided in the region of the diffusion layer 19. This ensures that the diffusion layer 19 is only exposed at the front face of the sensor.

Figure 3:
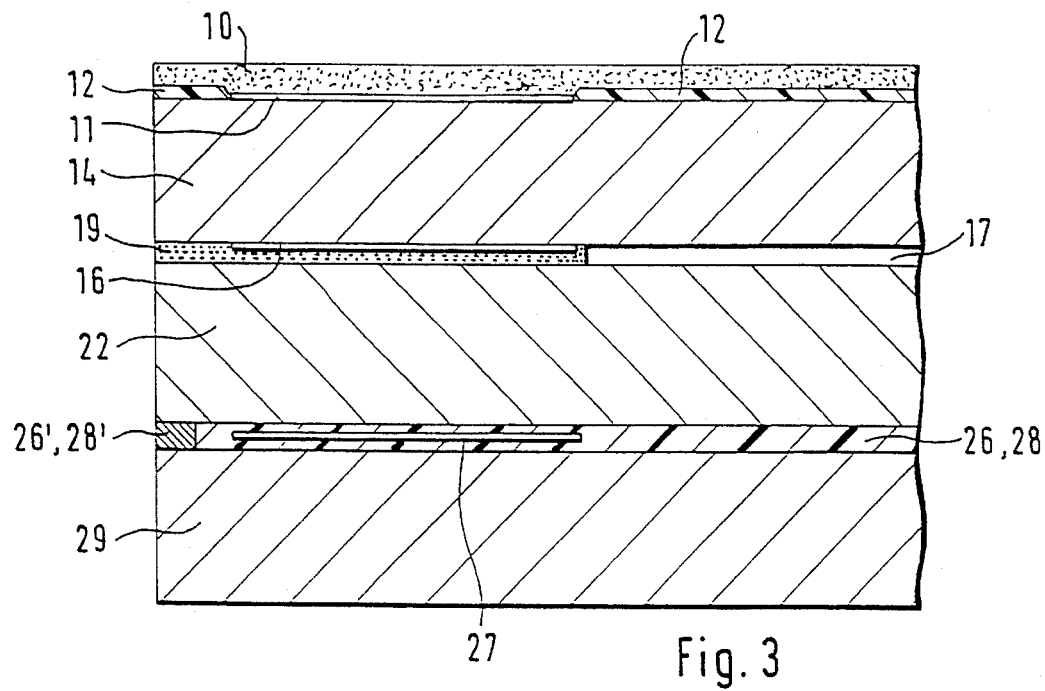
FIG. 3 shows a longitudinal section through the diffusion zone of the sensors according to FIGS. 1 and 2.

The lamination of pumping cell A, the thin intermediate layer B, and heating unit C by means of interlaminated bonding layers 20, 23, 24, the result after sintering is the first and second embodiment of the sensor as shown in a cutout in the region of diffusion layer 19 in the longitudinal section of FIG. 3. Both sensors are configured as slim sensors.

Figure 5:
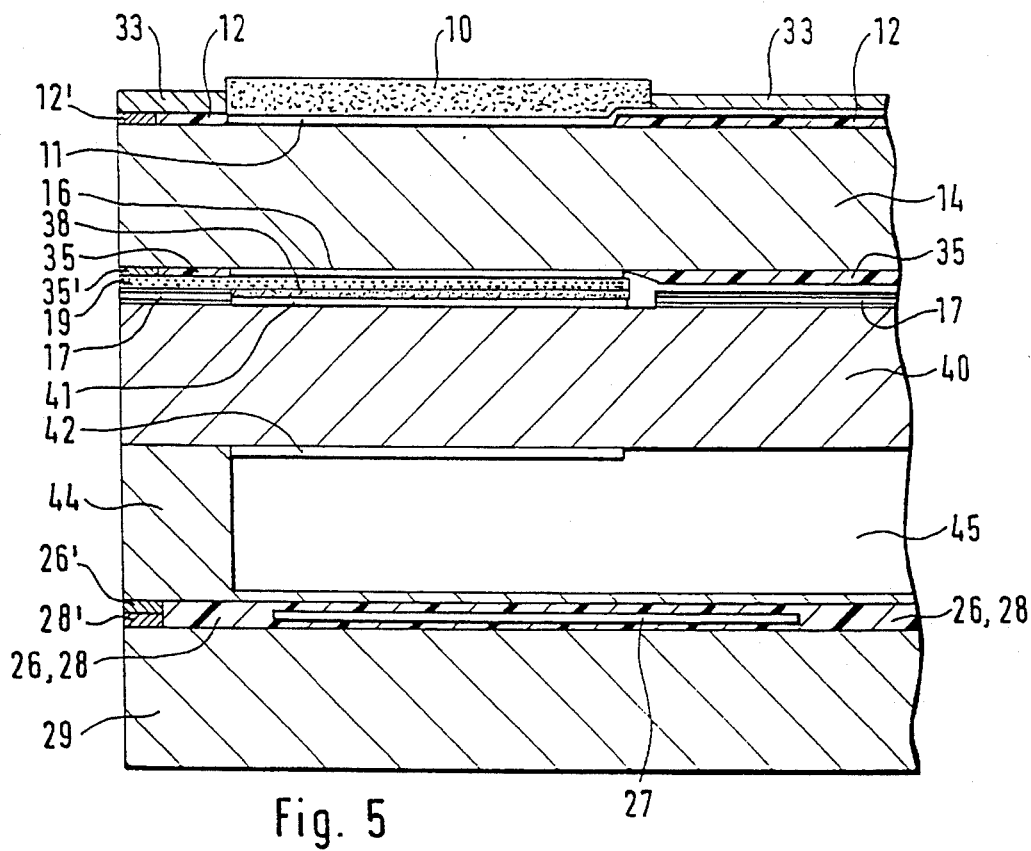
FIG. 5 shows a longitudinal section through the diffusion zone of the broad-band sensor according to FIG. 4.
Figure 4:
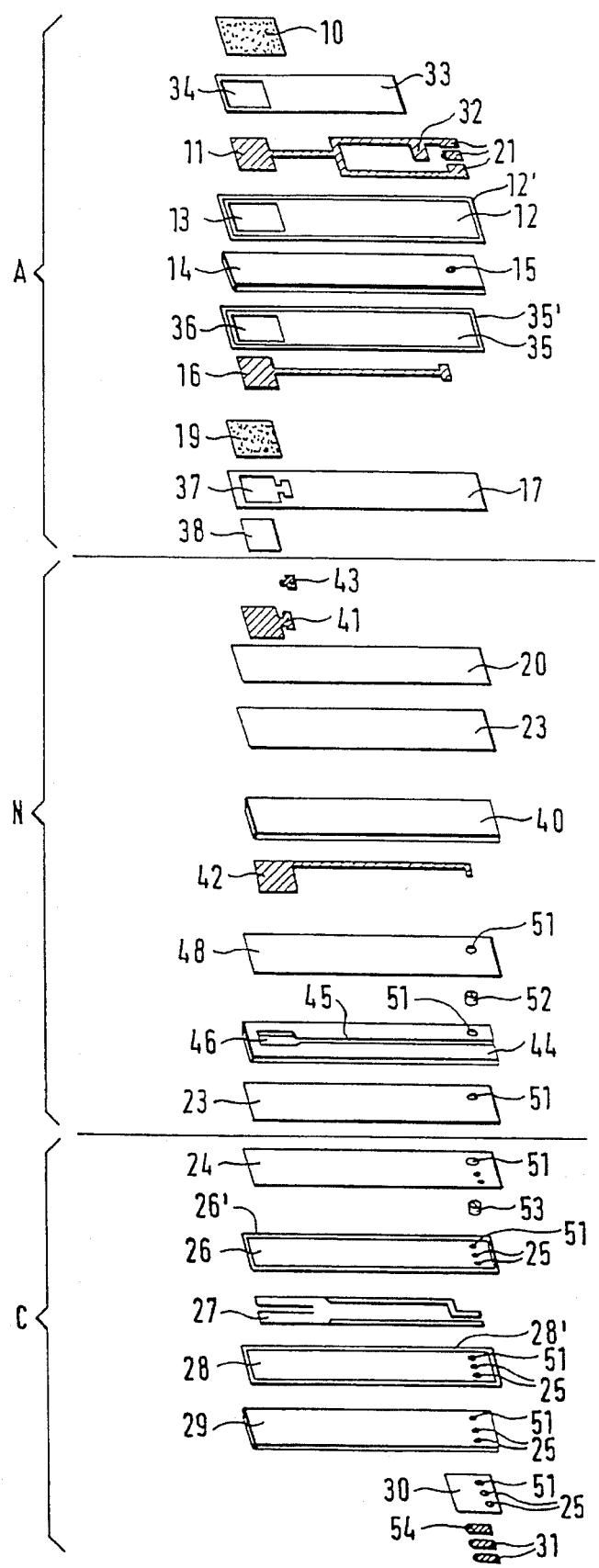
FIG. 4 shows the layout of a third embodiment of a sensor according to the invention which, in addition to being provided with a pumping cell and heating cell is provided with a Nernst cell and thus represents a broad-band sensor.

The third embodiment shown in FIGS. 4 and 5 relates to a sensor which is configured as a broad-band polarographic sensor, which is essentially different from the aforedescribed sensor in FIGS. 1 and 2 in that it is provided with a Nernst cell N in addition to pumping cell A and heating unit C.

The pumping cell A, according to the first and second embodiment, comprises a thin solid electrolyte sheet 14, the outer pumping electrode 11 including a trim resistance 32, and the inner pumping electrode 16. The insulation 12, including the gas tight frame 12', is disposed between the thin solid electrolyte sheet 14 and the outer pumping electrode 11. In the region of the electrode 11, a window 13 is provided in the insulation 12 such that the outer pumping electrode 11 makes contact with the thin solid electrolyte sheets 14. A cover layer 33, including a further window 34 which is inserted into the same, is disposed above the outer pumping electrode 11 such that the connectors 21 and the trim resistance 32 are freely accessible and the outer pumping electrode 11 is disposed on the interior of window 34. The cover layer 10 in this embodiment is placed over the window 34.

A further insulation 35 having a gas tight frame 35' is arranged between the thin solid electrolyte sheet 14 and the inner pumping electrode 16. The inner pumping electrode 16 is positioned within window 36. As in the first and second embodiment, the diffusion layer 19 is placed over the inner pumping electrode 16. The equalizing layer 17 is arranged over the diffusion layer 19 and over the region of the sensor which is not covered by the diffusion layer 19. The equalizing layer 17 in this case has a recess 37 whose purpose will be discussed in connection with the description of the Nernst cell N.

The Nernst cell N is made of a thin solid electrolyte sheet 40, a measuring electrode 41, a reference electrode 42, and a further thin solid electrolyte sheet 44 having a reference channel 45 and a reference gap 46. The measuring electrode 41 is positioned such that the pumping electrode 16 lies opposite the diffusion layer 19. In order to prevent an electrical contact in the region of the diffusion layer 19 a gas-tight insulation 38 is arranged between diffusion layer 19 and measuring electrode 41. Through this insulation, the measuring gas reaches the measuring electrode 41. The recess 37 set in the equalizing layer 17 serves to produce, by way of a contact 43, an electrical connection between the measuring electrode 41 and the inner pumping electrode 16 of pumping cell A. This makes clear that the measuring electrode 41 is applied to the inner pumping electrode 16 by way of contact 43, with the contact of the inner pumping electrode 16 being made by one of contacts 21 by way of the through-hole 15 set in the thin solid electrolyte sheet 14.

The reference electrode 42 is arranged at the lower side of the thin solid electrolyte sheet 40 and is in contact with reference gap 46. The reference atmosphere reaches the reference electrode 42 by way of reference channel 45 and reference gap 46. A further interlaminary bonding layer 48 is disposed between the two thin solid electrolyte sheets 40 and 44. Layers 20, 23, 24 are conventional interlaminated bonding layers by way of which the members of the sensor are laminated together. In order to contact the reference electrode 42, through-holes 51 are set in the lower one of the two layers 23 and into layer 48 as well as in the thin solid electrolyte sheet 44, respectively, with a connecting pin 52 being placed in each through-holes 51.

The heating unit C is configured similarly to the first two embodiments. The heating unit C thus comprises the thin solid electrolyte sheet 29, including through-holes 25, 51; the heater 27; the first insulation 26 in the direction of the Nernst cell N, including a gas tight frame 26'; the second insulation 28 also having the gas-tight frame 28'; the second insulation 30; the interlaminated bonding layer 24; and heater connectors 31.

Through-hole 51 provided for contacting the reference electrode 42 is also made through layer 24, the insulations 26 and 28 and the thin solid electrolyte sheet 29. Contacting holes 51 are provided so that the reference electrode 42 may be placed on the outside by means of connecting pin 53. The connection of the heating unit C to the Nernst cell results from laminating together layers 23 and 24.

The thin intermediate sheet B used in order to stabilize the sensor in the first and second embodiment is laminated in the third embodiment, since the Nernst cell N is already provided with two thin solid electrolyte sheets 40 and 44.

Figure 6:
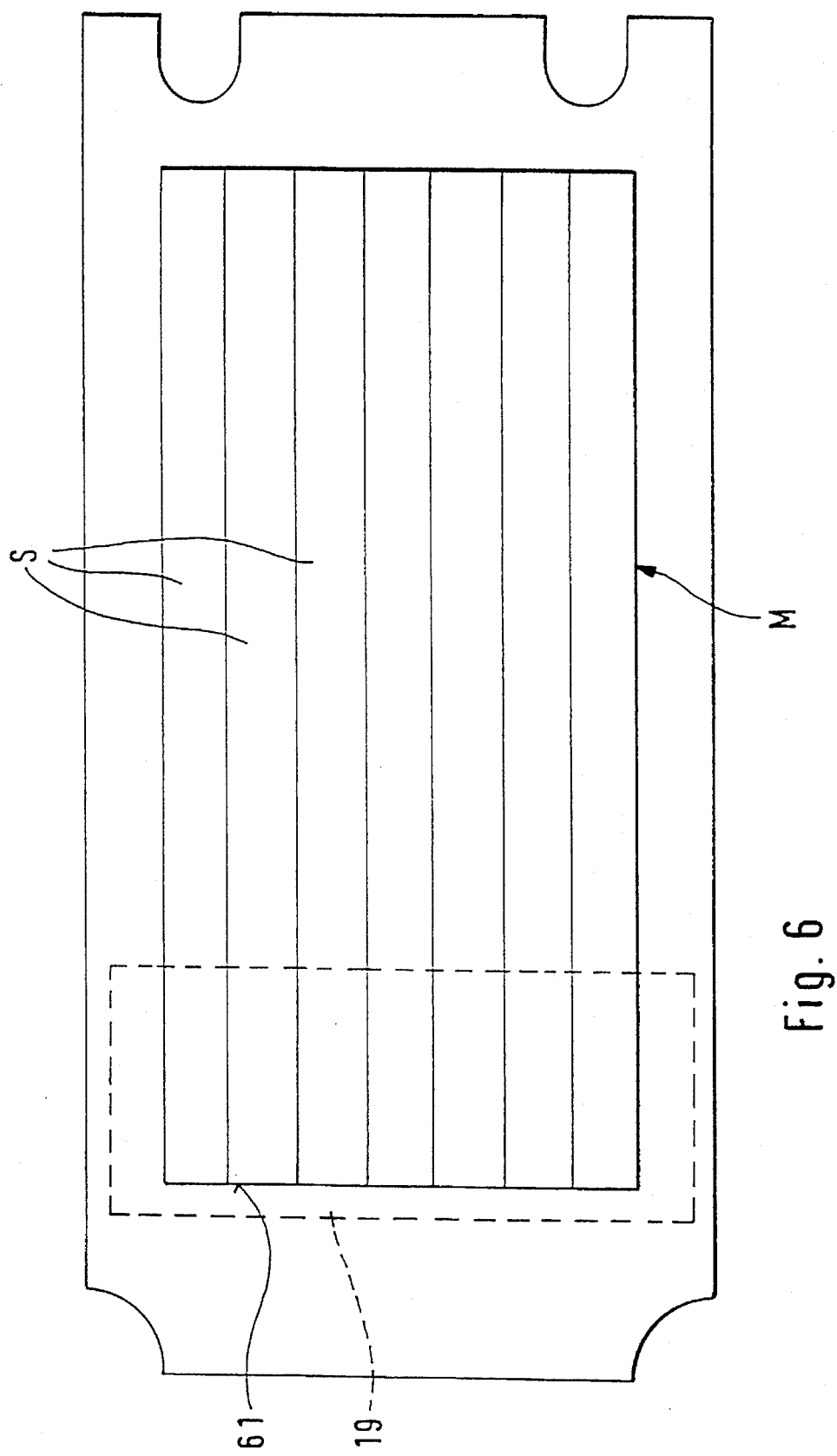
FIG. 6 shows a plan view of a multiple panel for the production of the sensor according to the invention.

The production of the polarographic sensor according to the invention is to be explained by way of the example schematically illustrated in FIGS. 1 and 3 and elucidated by way of the basic illustration of a multiple panel M (FIG. 6). The multiple panel M contains a plurality of panels S, which later form the polarographic sensors.

In order to produce pumping cell A, an approximately 0.3 to 0.6 mm thick $ZrO_2$ sheet having a $Y_2O_3$ stabilized sheet is used as a thin solid electrolyte sheet 14. The thin $ZrO_2$ sheet dimensioned such that a corresponding number of sensors may be placed next to one another resulting in a multiple panel having, for example, 7 panels according to FIG. 6.

The insulation 12, the outer and inner pumping electrode 11 and 16 and the associated conductors and connectors 21 are printed on the thin solid electrolyte sheet 14 by the screen printing method and by using a conventional Pt-cermet paste and protective layer 10. For the purpose of through-contacting, the through-hole 15 is also filled with the electrically conductive Pt-cermet layer.

The diffusion layer 19 is printed over the width of multiple panel M. In this regard, it is important for the diffusion layer 19 to project over the front edge 61 of panel S. Porous zirconium oxide, is used, for example, as diffusion layer 19, with the porosity of the diffusion layer 19 being produced by adding pore-forming substances which either combust, decompose or dissipate in the sintering process. Typical pore forming substances are, for example, thermal carbon black powder; plastics, for example, on a polyurethane base; salts, for example, ammonium carbonate; and organic substances such as, for example, theobromine and indanthrene blue. This type of pore-forming agent is added to the printing paste consisting of zirconium oxide in such quantities as to result in a diffusion layer having a 10 to 50% porosity. The average diameter of the pores is preferably between 5–50 micrometers.

The region of an individual panel S not provided with the diffusion layer 19 is subsequently printed on with the equalizing layer 17. And, finally, the multiple panel is coated with interlaminary binder 20.

The thin intermediary sheet B is produced in a second step, and heating unit C in a third step. The thin intermediary sheet B and the heating unit C is produced in a manner also known in the screen printing process.

The known $O_2$ ion-conducting thin solid electrolyte sheets on a base of oxides constituted of quadrivalent metals particularly such as $ZrO_2$, $CeO_2$, $HfO_2$ and $ThO_2$ having a content of bivalent alkaline earth oxide and/or, preferably, trivalent oxides of the noble earths.

The pumping electrodes and the associated strip conductors and connectors comprise, in a known manner, pastes on a noble earth metal base, particularly, platinum or the noble metal cermet. The heater 27 comprises the same material.

Subsequent to the production of multiple panels of the pumping cell A, the thin intermediate sheet E and the heating unit C, the three individual multiple panels are laminated together by means of the interlaminary binder layer 20, 23. Then, the individual sensors are cut out of the multiple panels. Due to the diffusion layer 19, which extends over the entire multiple panel, separation into panels S, results in exposing diffusion layer 19, according to the first embodiment, at the front face and the two side faces. These three faces form the diffusion barrier for the measuring gas.

In the second embodiment illustrated in FIG. 2, a diffusion layer 19 is printed on each panel S, with the diffusion layer 19 of each panel also projecting over the front edge of each panel S. The two side regions of the diffusion layer 19 of the individual panels S in this case are—as already explained in connection with description of FIG. 2—limited by equalizing layer 17. This causes the diffusion layer 19 only to be exposed at the front faces.

Subsequent to the separation of the multiple panel, panels S are sintered at a temperature of approximately 1,400° C. The sensor obtained in this manner may be mounted to known housings and may be used for determining the lambda value.

We claim:

1. A sensor arrangement which is a multiple printed panel, comprising:

a plurality of planar polarographic sensors for determining the lambda value of gas mixtures for use with exhaust gases in internal combustion engines disposed side by side, each sensor of the plurality of planar polarographic sensors being comprised of:

a planar ceramic carrier sheet having an outer pumping electrode and an inner pumping electrode respectively arranged on opposite planar sides thereof; and a diffusion barrier, wherein the outer and inner pumping electrodes, and the diffusion barrier are arranged on the planar ceramic carrier sheet so that measuring gas is fed via the diffusion barrier to the inner pumping electrode, wherein the sensor has front and side edge faces, and the diffusion barrier is configured as a diffusion layer which at least partially covers the inner pumping electrode and which is exposed to the measuring gas at least at one edge face of the sensor, and wherein a diffusion-free planar region of the sensor is provided with an equalizing layer having the same thickness as the diffusion layer, and the equalizing layer is disposed in the same plane with and adjacent to the diffusion layer; and wherein the diffusion layers of respective sensors collectively comprise a single common diffusion layer which extends over the entire width of the multiple printed panel and projects beyond the front edge faces of the plurality of sensors.

2. The sensor arrangement according to claim 1, wherein the diffusion-free planar region of the sensors comprises a single common diffusion-free planar region covered with an equalizing layer which extends over the entire multiple-printed panel.

3. A sensor arrangement which is a multiple printed panel, comprising:

a plurality of planar polarographic sensors for determining the lambda value of gas mixtures for use with exhaust gases in internal combustion engines disposed side by side, each sensor of the plurality of planar polarographic sensors being comprised of:

a planar ceramic carrier sheet having an outer pumping electrode and an inner pumping electrode respectively arranged on opposite planar sides thereof; and a diffusion barrier, wherein the outer and inner pumping electrodes, and the diffusion barrier are arranged on the planar ceramic carrier sheet so that measuring gas is fed via the diffusion barrier to the inner pumping electrode, wherein the sensor has front and side edge faces, and the diffusion barrier is configured as a diffusion layer which at least partially covers the inner pumping electrode and which is exposed to the measuring gas at least at one edge face of the sensor, wherein a diffusion-free planar region of the sensor is provided with an equalizing layer having the same thickness as the diffusion layer, and the equalizing layer is disposed in the same plane with and adjacent to the diffusion layer, and wherein the equalizing layer extends toward the front edge face of the sensor along two side edge faces of the sensor between the diffusion layer and the two side edge faces of the sensor up to the front edge face of the sensor, and the diffusion layer extends to the front edge face, such that the diffusion layer is exposed to the measuring gas along a part of the front edge face bounded by the equalizing layer; and wherein the diffusion layers of respective sensors collectively comprise a single common diffusion layer which projects over a front edge of the panel.

4. The sensor arrangement according to claim 3, wherein the diffusion-free planar regions of the sensors comprises a single common diffusion-free region, and wherein an equalizing layer covers the common diffusion-free free planar region of the multiple printed panel.

5. A method of producing a sensor arrangement which is a multiple printed panel comprised of:

a plurality of planar polarographic sensors for determining the lambda value of gas mixtures for use with exhaust gases in internal combustion engines disposed side by side, each sensor of the plurality of planar polarographic sensors, comprising:

a planar ceramic carrier sheet having an outer pumping electrode and an inner pumping electrode respectively arranged on opposite planar sides thereof; and a diffusion barrier, wherein the outer and inner pumping electrodes, and the diffusion barrier are arranged on the planar ceramic carrier sheet so that measuring gas is fed via the diffusion barrier to the inner pumping electrode, wherein the sensor has front and side edge faces, and the diffusion barrier is configured as a diffusion layer which at least partially covers the inner pumping electrode and which is exposed to the measuring gas at least at one edge face of the sensor, and wherein a diffusion-free planar region of the sensor is provided with an equalizing layer having the same thickness as the diffusion layer, and the equalizing layer is disposed in the same plane with and adjacent to the diffusion layer; and wherein the diffusion layers of respective sensors collectively comprise a single common diffusion layer which extends over the entire width of the multiple printed panel and projects beyond the front edge faces of the plurality of sensors, the method comprising:

providing a plurality of individual ceramic carriers;

providing outer and inner pumping electrodes arranged on the respective ceramic carriers;

forming a multiple printed panel by joining on a substrate the plurality of individual ceramic carriers arranged side by side with front edges thereof parallel and in line so that the carriers are adjacent to one another;

providing a diffusion layer which projects beyond at least the front edge of the individual ceramic carriers; and providing the diffusion-free planar region of the multiple printed panel with an equalizing layer of approximately the thickness of the diffusion layer.

6. The method according to claim 5, wherein the step of providing the diffusion layer comprises providing the diffusion layer so that it projects over the entire surface of the front edge and over the two side edges of the individual ceramic carriers.

7. The method according to claim 5, wherein the step of providing the diffusion layer comprises providing the diffusion layer so that each ceramic carrier is provided with a section of the diffusion layer which projects over the front edge of the individual ceramic carrier and so that at the respective side edge faces of each ceramic carrier at least a narrow diffusion-free strip is provided.

* * * * *